US009834820B2

(12) United States Patent
Cormier-Daire et al.

(10) Patent No.: US 9,834,820 B2
(45) Date of Patent: Dec. 5, 2017

(54) METHODS FOR THE TREATMENT AND DIAGNOSIS OF BONE MINERAL DENSITY RELATED DISEASES

(71) Applicants: INSERM (Institut National de la Sante et de la Recherche Medicale), Paris (FR); UNIVERSITE PARIS DESCARTES, Paris OT (FR); ASSISTANCE PUBLIQUE-HOPITAUX DE PARIS (AP-HP), Paris OT (FR)

(72) Inventors: Valerie Cormier-Daire, Paris (FR); Arnold Munnich, Paris (FR)

(73) Assignees: INSERM (Institut National de la Sante et de la Recherche Medicale), Paris (FR); Universite Paris Descartes, Paris (FR); Assistance Publique—Hopitaux de Paris (AP-HP), Paris (FR)

( * ) Notice: Subject to any disclaimer, the term of this patent is extended or adjusted under 35 U.S.C. 154(b) by 0 days.

(21) Appl. No.: 14/577,177

(22) Filed: Dec. 19, 2014

(65) Prior Publication Data
US 2015/0104437 A1    Apr. 16, 2015

Related U.S. Application Data

(63) Continuation of application No. 12/746,456, filed as application No. PCT/EP2008/066880 on Dec. 5, 2008, now abandoned.

(30) Foreign Application Priority Data

Dec. 7, 2007    (EP) ..................................... 07301643

(51) Int. Cl.
  C12Q 1/68      (2006.01)
  A61K 31/357    (2006.01)
  A61K 38/52     (2006.01)

(52) U.S. Cl.
  CPC .......... *C12Q 1/6883* (2013.01); *A61K 31/357* (2013.01); *A61K 38/52* (2013.01);
  (Continued)

(58) Field of Classification Search
  CPC ............ C12Q 1/6883; C12Q 2600/136; C12Q 2600/156; C12Y 503/99005; A61K 31/357; A61K 38/52
  See application file for complete search history.

(56) References Cited

U.S. PATENT DOCUMENTS

2008/0090830 A1*   4/2008   Chackalamannil .. C07D 417/06
                                                            514/248
2010/0284991 A1    11/2010  Cormier-Daire

FOREIGN PATENT DOCUMENTS

WO            97/05275        2/1997

OTHER PUBLICATIONS

Database Medline [Online], US National Library of Medicine (NLM), Bethesda, MD, US, XP002471981, 2008.
(Continued)

Primary Examiner — Reza Ghafoorian
(74) Attorney, Agent, or Firm — Whitham Curtis & Cook, PC

(57) ABSTRACT

Described herein are methods of the treatment and diagnosis of bone mineral density related disorders. More particularly, described herein are methods of diagnosing or predicting a bone mineral density related disease, or a risk of a bone mineral density related disease, in a subject, which method comprises detecting a mutation in the TBXAS1 gene, wherein the presence of such a mutation is indicative of a
(Continued)

Figure 1:
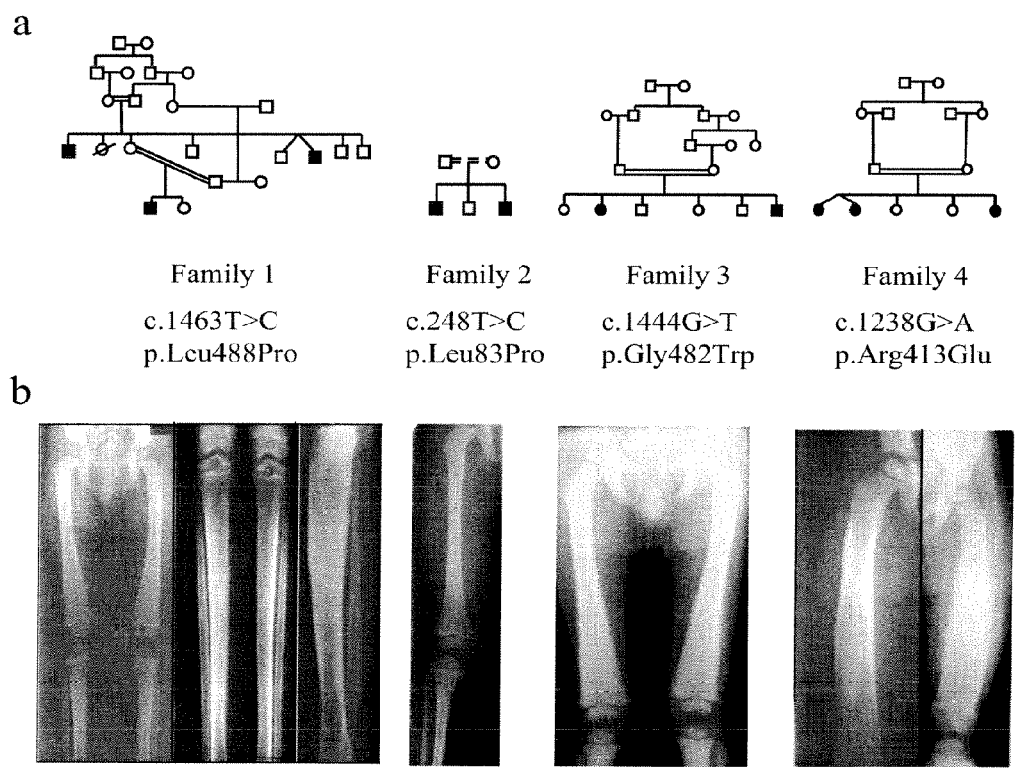

bone mineral density related disease or of a risk of a bone mineral density related disease. Also described are compounds such as a thromboxane synthase (TXAS) encoding polynucleotide, a TXAS, thromboxane A2 or an analog thereof for treating or preventing a disease associated with an increased bone mineral density (e.g., Ghosal hematodiaphyseal dysplasia syndrome). Additional aspects describe an inhibitor of TBXAS1 gene expression or a thromboxane inhibitor for treating or preventing a disease associated with a decreased bone mineral density (e.g., osteoporosis).

2 Claims, 5 Drawing Sheets

(52) U.S. Cl.
CPC .. *C12Q 2600/136* (2013.01); *C12Q 2600/156* (2013.01); *C12Y 503/99005* (2013.01)

(56) References Cited

OTHER PUBLICATIONS

International Search Report and Written Opinion in PCT/EP08/66880, dated Feb. 3, 2009.
Genevive et al., "Thromboxane synthase mutations in an increased bone density disorder (Ghosal syndrome)," Nature Genetics, 40(3):284-286 (2008).

* cited by examiner

METHODS FOR THE TREATMENT AND DIAGNOSIS OF BONE MINERAL DENSITY RELATED DISEASES

The present application is filed as a continuation of U.S. patent application Ser. No. 12/746,456, which was filed Jun. 4, 2010, which was filed pursuant to 35 U.S.C. 371 as a U.S. National Phase application of International Patent Application No. PCT/EP08/66880, which was filed Dec. 5, 2008, claiming the benefit of priority to European Patent Application No. 07301643.8, which was filed on Dec. 7, 2007. The entire text of the aforementioned applications is incorporated herein by reference in its entirety.

FIELD OF THE INVENTION

The present invention relates to methods for the treatment and diagnosis of bone mineral density related disorders. More particularly, the present invention is based on the discovery that thromboxane synthase plays a role in bone mineral density variation.

BACKGROUND OF THE INVENTION

Vertebral bone quality is essential in vertebral strength. A major factor of bone quality is the bone mineral density and its distribution throughout the bone and several evidences now show that bone mineral density impacts several human conditions.

Osteoporosis, or porous bone, is a disease characterized by low bone mineral density, leading to bone fragility and an increased susceptibility to fractures, especially of the hip, spine and wrist, although any bone can be affected. If not prevented or if left untreated, osteoporosis can progress painlessly until a bone breaks. It is estimated that Osteoporosis is responsible for more than 1.5 million fractures annually, including over 300,000 hip fractures; and approximately 700,000 vertebral fractures; 250,000 wrist fractures; and 300,000 fractures at other sites. Genetic factors play an important role in the pathogenesis of osteoporosis and several studies suggest that between 50%-85% of the variance in bone mineral density is genetically determined (Gueguen et al. 1995; Arden and Spector 1997). However the genes responsible for these effects are incompletely defined. Most agents used to treat osteoporosis, such as estrogens and bisphosphonates, are not very effective. These agents retard bone resorption but do not improve connectivity. Therefore there is a permanent need to provide new targets for the treatment of osteoporosis.

A contrario, bone mineral density has been shown to be increased in several other pathologies or conditions. For example, increased bone mineral density has been shown in postmenopausal females with postthyroidectomy hypoparathyroidism. Moreover, several drugs have been shown to induce increased bone mineral density. For example, twelve month results from a Phase IIB study with odanacatib, (formerly MK-0822), an investigational selective inhibitor of cathespin-K, demonstrated dose-dependent increases in bone mineral density and reduced bone turnover compared to placebo in postmenopausal women (29th Annual Meeting of the American Society for Bone and Mineral Research (ASBMR)). Another example includes the Ghosal hematodiaphyseal dysplasia syndrome (GHDD) which is a rare autosomal recessive disorder characterized by increased bone mineral density with predominant diaphyseal involvement, aregenerative corticosensitive anemia and chronic biological inflammation (Ghosal et al. 1988).

Therefore, there is an existing need to identify factors which impact the bone mineral density so as to envisage methods for diagnosing, predicting, preventing and treating bone mineral density related diseases.

A wide variety of candidate genes have been studied so far in relation to bone mineral density, including the vitamin D receptor (Kelly P J et al. 1997) and the estrogen receptor (Kobayashi et al. 1996). Current evidence suggests that allelic variation in these genes accounts for only a small portion of the variance in bone mineral density however (Rubin et al. 1999) indicating that most of the genes which regulate bone mineral density remain to be discovered. The identification and genotyping of polymorphisms associated with regulation of bone mineral density is useful, to define markers of bone mass and hence, for example, susceptibility to bone mineral density related diseases.

SUMMARY OF THE INVENTION

The present invention relates to a method of diagnosing or predicting a bone mineral density related disease, or a risk of a bone mineral density related disease, in a subject, which method comprises detecting a mutation in the TBXAS1 gene, wherein the presence of said mutation is indicative of a bone mineral density related disease or of a risk of a bone mineral density related disease, wherein said method comprises the step of detecting a TBXAS1 mutation in a nucleic acid sample obtained from said subject.

The invention also relates to a compound selected from the group consisting of a thromboxane synthase (TXAS) encoding polynucleotide, TXAS, thromboxane A2 or an analog thereof for treating or preventing a disease associated with an increased bone mineral density (e.g., Ghosal hematodiaphyseal dysplasia syndrome).

The invention also relates to a compound selected from the group consisting of an inhibitor of TBXAS1 gene expression or a thromboxane inhibitor for treating or preventing a disease associated with a decreased bone mineral density (e.g., osteoporosis).

DETAILED DESCRIPTION OF THE INVENTION

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences. As used herein, the term "TBXAS1 gene" denotes the thromboxane synthase gene of any species, especially human, but also other mammals or vertebrates to which the methods of the invention can apply. The TBXAS1 gene encodes a 60 kDa transmembrane thromboxane synthase ("TXAS"). *Homo sapiens* TBXAS1 gene is localized on chromosome 7 (location 7q34-q35), the sequence of which is deposited in Genebank under accession number NC_000007.12.

The TBXAS1 gene encodes a transcript deposited in GeneBank under accession number NM_001061, which contains the open-reading frame as set forth in SEQ ID No:1. The corresponding amino acid sequence is deposited in GenPept database under accession number NP_001052 and is set forth in SEQ ID No:2.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989).

The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., 1989, 9.50-9.51). For hybridization with shorter nucleic acids, i.e., oligonucleotides, the position of mismatches becomes more important, and the length of the oligonucleotide determines its specificity (see Sambrook et al., 1989 II.7-11.8). A minimum length for a hybridizable nucleic acid is at least about 10 nucleotides, preferably at least about 15 nucleotides, and more preferably the length is at least about 20 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, an amplification primer is an oligonucleotide for amplification of a target sequence by extension of the oligonucleotide after hybridization to the target sequence or by ligation of multiple oligonucleotides which are adjacent when hybridized to the target sequence. At least a portion of the amplification primer hybridizes to the target. This portion is referred to as the target binding sequence and it determines the target-specificity of the primer. In addition to the target binding sequence, certain amplification methods require specialized non-target binding sequences in the amplification primer. These specialized sequences are necessary for the amplification reaction to proceed and typically serve to append the specialized sequence to the target. For example, the amplification primers used in Strand Displacement Amplification (SDA) include a restriction endonuclease recognition site 5' to the target binding sequence (U.S. Pat. No. 5,455,166 and U.S. Pat. No. 5,270,184). Nucleic Acid Based Amplification (NASBA), self-sustaining sequence replication (3SR) and transcription based amplification primers require an RNA polymerase promoter linked to the target binding sequence of the primer. Linking such specialized sequences to a target binding sequence for use in a selected amplification reaction is routine in the art. In contrast, amplification methods such as PCR which do not require specialized sequences at the ends of the target, generally employ amplification primers consisting of only target binding sequence.

As used herein, the terms "primer" and "probe" refer to the function of the oligonucleotide. A primer is typically extended by polymerase or ligation following hybridization to the target but a probe typically is not. A hybridized oligonucleotide may function as a probe if it is used to capture or detect a target sequence, and the same oligonucleotide may function as a primer when it is employed as a target binding sequence in an amplification primer. It will therefore be appreciated that any of the target binding sequences disclosed herein for amplification, detection or quantisation of TBXAS1 may be used either as hybridization probes or as target binding sequences in primers for detection or amplification, optionally linked to a specialized sequence required by the selected amplification reaction or to facilitate detection.

The terms "mutant" and "mutation" mean any detectable change in genetic material, e.g. DNA, RNA, cDNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence. Generally a mutation is identified in a subject by comparing the sequence of a nucleic acid or polypeptide expressed by said subject with the corresponding nucleic acid or polypeptide expressed in a control population. A mutation in the genetic material may also be "silent", i.e. the mutation does not result in an alteration of the amino acid sequence of the expression product.

In the context of the instant application, mutations identified in TBXAS1 gene are designated pursuant to the nomenclature of Dunnen and Antonarakis (2000). As defined by Dunnen and Antonarakis at the nucleic acid level, substitutions are designated by ">", e.g. "1463T>C" denotes that at nucleotide 1463 of the reference sequence a T is changed to a C. When the full-length genomic sequence is known, the mutation is best designated by the nucleotide number of the genomic references. The nucleic acid mutations are designated by reference to the nucleotide number in SEQ ID No:1.

The term "sequence similarity" in all its grammatical forms refers to the degree of identity or correspondence between nucleic acid or amino acid sequences of proteins that may or may not share a common evolutionary origin. Preferably the degree of sequence identity is calculated compared with the totality of a reference sequence.

In a specific embodiment, two DNA sequences are "substantially homologous" or "substantially similar" when at least 70%, preferably at least 75% or 80% or 85% or 90% or 95% or 99%, of the nucleotides match over the defined length of the DNA sequences, as determined by sequence comparison algorithms, such as BLAST, FASTA, DNA Strider, etc. An example of such a sequence is an allelic or species variant of TBXAS1 gene. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially similar" when greater than 80%, preferably than 85% or 90% or 95% or 99%, of the amino acids are similar (functionally identical). "Functionally identical" polypeptides are those in which a given amino acid residue has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Preferably, the similar sequences are identified by alignment using, for example, the GCG (Genetics Computer Group, Program Manual for the GCG Package, Version 7, Madison, Wis.) pileup program, or any of the programs described above (BLAST, FASTA, etc.).

"Thromboxane inhibitor" includes compounds which are the so-called thromboxane A2 receptor antagonists, thromboxane A2 antagonists, thromboxane A2/prostaglandin endoperoxide antagonists, thromboxane receptor (TP) antagonists, thromboxane antagonists, thromboxane synthase inhibitors, and dual acting thromboxane synthase inhibitors and thromboxane receptor antagonists.

"Thromboxane A2 receptor antagonist" refers to any compound that reversibly or irreversibly blocks the activation of any thromboxane A2 receptor.

"Thromboxane synthase inhibitor" refers to any compound that reversibly or irreversibly inhibits the enzyme thromboxane synthase thereby reducing the formation of thromboxane A2.

"Dual acting thromboxane receptor antagonist and thromboxane synthase inhibitor" refers to any compound that simultaneously acts as a thromboxane A2 receptor antagonist and a thromboxane synthase inhibitor.

The term "bone mineral density related diseases" encompasses all disorders that are associated with, caused by, or result from bone mineral density variation: a decrease or an increase in comparison with a control population. More particularly, a "disease associated with a decreased bone mineral density" denotes a disease that is associated with, caused by, or results from a decrease in bone mineral density. More particularly, a "disease associated with an increased bone mineral density" denotes a disease that is associated with, caused by, or results from an increase in bone mineral density.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent (e.g., TBXAS1 polynucleotide, or thromboxane synthase inhibitor) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

The term "biological sample" means any biological sample derived from a patient. Examples of such samples include fluids, tissues, cell samples, organs, biopsies, etc. Preferred biological samples are a cell or tissue sample. Preferred biological samples are whole blood, serum, plasma or urine.

As used herein, the term "subject" denotes a mammal, such as a rodent, a feline, a canine, and a primate. Preferably a subject according to the invention is a human.

The expression "mutation in the TBXAS1 gene associated with a decrease of the Thromboxane synthase activity" encompasses mutations which result in a decreased expression level of the TBXAS1 gene and mutations which result in the synthesis of TXAS which displays a decreased enzymatic activity, i.e., a decreased convertion of prostaglandins (PG) H2 into Thromboxane A2 (TXA2)

The expression "mutation in the TBXAS1 gene associated with an increase of the Thromboxane synthase activity" encompasses mutations which result in a increased expression level of the TBXAS1 gene and mutations which result in the synthesis of TXAS which displays an increased enzymatic activity, i.e., an increased convertion of prostaglandins (PG) H2 into Thromboxane A2 (TXA2)

Mutations in TBXAS1 Gene

The inventors identified various mutations in the TBXAS1 gene. As shown in example, direct sequencing of the TBXAS1 gene has led to the detection of distinct homozygous missense mutations in all four GHDD families of Example: 1463T>C, 248T>C, 1444G>T and 1238G>A, by reference to the nucleotide numbers of SEQ ID No 1.

A nucleic acid comprising a TBXAS1 nucleotide sequence, or a fragment thereof, carrying a mutation such as defined above is part of the invention.

Accordingly, the invention relates to an isolated nucleic acid encoding the TXAS, which nucleic acid comprises or consists in a TBXAS1 gene sequence that contains a mutation selected from the group consisting of 1463T>C, 248T>C, 1444G>T and 1238G>A. Said nucleic acid may contains one or more of the above mutations.

The invention further relates to the polypeptide encoded by said nucleic acid. More specifically, the mutations 1463T>C, 248T>C, 1444G>T and 1238G>A in the TBXAS1 gene result in Leu488Pro, Leu83Pro, Gly482Trp and Arg413Glu mutants of TXAS respectively. The amino acid positions are indicated by reference to the polypeptide sequences as set forth in SEQ ID No:2

Accordingly, the invention further provides an isolated polypeptide which comprises or consists in the polypeptide sequence of TXAS containing a mutation selected from the group consisting of a Leu488Pro, Leu83Pro, Gly482Trp and Arg413Glu. Said polypeptide may contain one or more of the above mutations.

Diagnostic Methods of the Invention

The inventors have further shown that mutations found in TBXAS1 gene associated with a decrease of the Thromboxane synthase activity are associated with a disease associated with an increased bone mineral density, Ghosal hematodiaphyseal dysplasia syndrome (GHDD) in particular.

Therefore, the invention provides a method for diagnosing or predicting Ghosal hematodiaphyseal dysplasia syndrome, or a risk of Ghosal hematodiaphyseal dysplasia syndrome, in a subject, which method comprises detecting a mutation in TBXAS1 gene, as compared to a control population, wherein the presence of a mutation is indicative of Ghosal hematodiaphyseal dysplasia syndrome or of a risk of Ghosal hematodiaphyseal dysplasia syndrome.

Without to be bound by any theory, the inventors believe that the TBXAS1 gene plays a role in the pathogenesis of bone mineral density related diseases.

Accordingly, an object of the invention relates to a method for diagnosing or predicting a bone mineral density related disease, or a risk of a bone mineral density related disease, in a subject, which method comprises detecting a mutation in TBXAS1 gene, as compared to a control population, wherein the presence of a mutation is indicative of a bone mineral density related disease or of a risk of a bone mineral density related disease.

In a particular embodiment, the bone mineral density related disease is selected in the group consisting of Ghosal hematodiaphyseal dysplasia syndrome, or osteoporosis.

According to a first embodiment, said mutation may be detected by analyzing a TBXAS1 nucleic acid molecule. In the context of the invention, TBXAS1 nucleic acid molecules include mRNA, genomic DNA and cDNA derived from mRNA. DNA or RNA can be single stranded or double stranded. These may be utilized for detection by amplification and/or hybridization with a probe, for instance.

Thus the invention provides a method of diagnosing or predicting a bone mineral density related disease, or a risk of a bone mineral density related disease, in a subject, which method comprises detecting a mutation in the TBXAS1 gene, wherein the presence of said mutation is indicative of a bone mineral density related disease or of a risk of a bone mineral density related disease, wherein said method comprises the step of detecting a TBXAS1 mutation in a nucleic acid sample obtained from said subject.

The nucleic acid sample may be obtained from any cell source or tissue biopsy. Non-limiting examples of cell sources available include without limitation blood cells, buccal cells, epithelial cells, fibroblasts, or any cells present in a tissue obtained by biopsy. Cells may also be obtained from body fluids, such as blood, plasma, serum, lymph, etc. DNA may be extracted using any methods known in the art, such as described in Sambrook et al., 1989. RNA may also be isolated, for instance from tissue biopsy, using standard methods well known to the one skilled in the art such as guanidium thiocyanate-phenol-chloroform extraction.

A TBXAS1 mutation according to the invention may be found in a regulating region of TBXAS1 gene (e.g. a promoter sequence, or a binding site for transcription factor), in introns of TBXAS1 gene or in exons that encode TXAS.

Preferably, a mutation of TBXAS1 gene according to the invention is selected from the group consisting of 1463T>C, 248T>C, 1444G>T and 1238G>A.

TBXAS1 mutations may be detected in a RNA or DNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a mutated site or that enable amplification of a region containing the mutated site. According to a first alternative, conditions for primer annealing may be chosen to ensure specific reverse transcription (where appropriate) and amplification; so that the appearance of an amplification product be a diagnostic of the presence of a particular TBXAS1 mutation. Otherwise, RNA may be reverse-transcribed and amplified, or DNA may be amplified, after which a mutated site may be detected in the amplified sequence by hybridization with a suitable probe or by direct sequencing, or any other appropriate method known in the art. For instance, a cDNA obtained from RNA may be cloned and sequenced to identify a mutation in TBXAS1 sequence.

Actually numerous strategies for genotype analysis are available (Antonarakis et al., 1989; Cooper et al., 1991; Grompe, 1993). Briefly, the nucleic acid molecule may be tested for the presence or absence of a restriction site. When a base substitution mutation creates or abolishes the recognition site of a restriction enzyme, this allows a simple direct PCR test for the mutation. Further strategies include, but are not limited to, direct sequencing, restriction fragment length polymorphism (RFLP) analysis; hybridization with allele-specific oligonucleotides (ASO) that are short synthetic probes which hybridize only to a perfectly matched sequence under suitably stringent hybridization conditions; allele-specific PCR; PCR using mutagenic primers; ligase-PCR, HOT cleavage; denaturing gradient gel electrophoresis (DGGE), temperature denaturing gradient gel electrophoresis (TGGE), single-stranded conformational polymorphism (SSCP) and denaturing high performance liquid chromatography (Kuklin et al., 1997). Direct sequencing may be accomplished by any method, including without limitation chemical sequencing, using the Maxam-Gilbert method; by enzymatic sequencing, using the Sanger method; mass spectrometry sequencing; sequencing using a chip-based technology; and real-time quantitative PCR. Preferably, DNA from a subject is first subjected to amplification by polymerase chain reaction (FOR) using specific amplification primers. However several other methods are available, allowing DNA to be studied independently of PCR, such as the rolling circle amplification (RCA), the Invader™ assay, or oligonucleotide ligation assay (OLA). OLA may be used for revealing base substitution mutations. According to this method, two oligonucleotides are constructed that hybridize to adjacent sequences in the target nucleic acid, with the join sited at the position of the mutation. DNA ligase will covalently join the two oligonucleotides only if they are perfectly hybridized.

Therefore, useful nucleic acid molecules, in particular oligonucleotide probes or primers, according to the present invention include those which specifically hybridize the regions where the mutations are located.

Oligonucleotide probes or primers may contain at least 10, 15, 20 or 30 nucleotides. Their length may be shorter than 400, 300, 200 or 100 nucleotides.

According to a second embodiment said mutation in the TBXAS1 gene may be detected at the protein level.

Accordingly, a mutation of TXAS according to the invention is preferably selected from the group consisting of mutations which result in Leu488Pro, Leu83Pro, Gly482Trp and Arg413Glu mutants of TXAS.

Said mutation may be detected according to any appropriate method known in the art. In particular a sample, such as a tissue biopsy, obtained from a subject may be contacted with antibodies specific of the mutated form of TXAS, i.e. antibodies that are capable of distinguishing between a mutated form of TBXAS1 and the wild-type protein (or any other protein), to determine the presence or absence of a TBXAS1 specified by the antibody.

Antibodies that specifically recognize a mutated TXAS also make part of the invention. The antibodies are specific of mutated TXAS, that is to say they do not cross-react with the wild-type TXAS.

The antibodies of the present invention may be monoclonal or polyclonal antibodies, single chain or double chain, chimeric antibodies, humanized antibodies, or portions of an immunoglobulin molecule, including those portions known in the art as antigen binding fragments Fab, Fab', F(ab')2 and F(v). They can also be immunoconjugated, e.g. with a toxin, or labelled antibodies.

Whereas polyclonal antibodies may be used, monoclonal antibodies are preferred for they are more reproducible in the long run.

Procedures for raising "polyclonal antibodies" are also well known. Polyclonal antibodies can be obtained from serum of an animal immunized against the appropriate antigen, which may be produced by genetic engineering for example according to standard methods well-known by one skilled in the art. Typically, such antibodies can be raised by administering mutated TXAS subcutaneously to New Zealand white rabbits which have first been bled to obtain pre-immune serum. The antigens can be injected at a total volume of 100 µl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988) which is hereby incorporated in the references.

A "monoclonal antibody" in its various grammatical forms refers to a population of antibody molecules that contains only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Laboratory methods for preparing monoclonal antibodies are well known in the art (see, for example, Harlow et al., 1988). Monoclonal antibodies (mAbs) may be prepared by immunizing purified mutated TXAS into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al.

Antibody generation techniques not involving immunisation are also contemplated such as for example using phage display technology to examine naive libraries (from non-immunised animals); see Barbas et al. (1992), and Waterhouse et al. (1993).

Antibodies raised against mutated TXAS may be cross reactive with wild-type TXAS. Accordingly a selection of antibodies specific for mutated TXAS is required. This may be achieved by depleting the pool of antibodies from those that are reactive with the wild-type TXAS, for instance by submitting the raised antibodies to an affinity chromatography against wild-type TXAS.

Alternatively, binding agents other than antibodies may be used for the purpose of the invention. These may be for instance aptamers, which are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Probe, primers, aptamers or antibodies of the invention may be labelled with a detectable molecule or substance, such as a fluorescent molecule, a radioactive molecule or any others labels known in the art. Labels are known in the art that generally provide (either directly or indirectly) a signal.

The term "labelled", with regard to the probe, primers, aptamers or antibodies of the invention, is intended to encompass direct labelling of the probe, primers, aptamers or antibodies of the invention by coupling (i.e., physically linking) a detectable substance to the probe, primers, aptamers or antibodies of the invention, as well as indirect labeling of the probe, primers, aptamers or antibodies of the invention by reactivity with another reagent that is directly labeled. Other examples of detectable substances include but are not limited to radioactive agents or a fluorophore (e.g. fluorescein isothiocyanate (FITC) or phycoerythrin (PE) or Indocyanine (Cy5)). Examples of indirect labeling include detection of a primary antibody using a fluorescently labeled secondary antibody and end-labeling of a DNA probe with biotin such that it can be detected with fluorescently labeled streptavidin. An antibody or aptamer of the invention may be labelled with a radioactive molecule by any method known in the art. For example radioactive molecules include but are not limited radioactive atom for scintigraphic studies such as I123, I124, In111, Re186, Re188.

Kits of the Invention

According to another aspect of the invention, the TBXAS1 mutation is detected by contacting the DNA of the subject with a nucleic acid probe, which is optionally labeled.

Primers may also be useful to amplify or sequence the portion of the TBXAS1 gene containing the mutated positions of interest.

Such probes or primers are nucleic acids that are capable of specifically hybridizing with a portion of the TBXAS1 gene sequence containing the mutated positions of interest. That means that they are sequences that hybridize with the portion mutated TBXAS1 nucleic acid sequence to which they relate under conditions of high stringency.

The present invention further provides kits suitable for determining at least one of the mutations of the TBXAS1 gene.

The kits may include the following components:

(i) a probe, usually made of DNA, and that may be pre-labelled. Alternatively, the probe may be unlabelled and the ingredients for labelling may be included in the kit in separate containers; and (ii) hybridization reagents: the kit may also contain other suitably packaged reagents and materials needed for the particular hybridization protocol, including solid-phase matrices, if applicable, and standards.

In another embodiment, the kits may include:

(i) sequence determination or amplification primers: sequencing primers may be pre-labelled or may contain an affinity purification or attachment moiety; and (ii) sequence determination or amplification reagents: the kit may also contain other suitably packaged reagents and materials needed for the particular sequencing amplification protocol. In one preferred embodiment, the kit comprises a panel of sequencing or amplification primers, whose sequences correspond to sequences adjacent to at least one of the polymorphic positions, as well as a means for detecting the presence of each polymorphic sequence.

In a particular embodiment, it is provided a kit which comprises a pair of nucleotide primers specific for amplifying all or part of the TBXAS1 gene comprising at least one of mutations that are identified herein, especially positions 1463, 248, 1444 and 1238.

Alternatively, the kit of the invention may comprise a labelled compound or agent capable of detecting the mutated polypeptide of the invention (e.g., an antibody or aptamers as described above which binds the polypeptide). For example, the kit may comprise (1) a first antibody (e.g., attached to a solid support) which binds to a polypeptide comprising a mutation of the invention; and, optionally, (2) a second, different antibody which binds to either the polypeptide or the first antibody and is conjugated to a detectable agent.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a bone mineral density related disease.

Therapeutic Methods of the Invention

In a further object, the invention relates to use, methods and pharmaceutical compositions for treating or preventing bone mineral density related diseases.

In a particular embodiment, the bone mineral density related disease is associated with increased bone mineral density. Examples of such diseases include but are not limited to Ghosal hematodiaphyseal dysplasia syndrome (GHDD).

Thus the invention further relates to a method for treating or preventing a disease associated with an increased bone mineral density which comprises the step of administering a subject in need thereof with a TBXAS1 polynucleotide, i.e. a nucleic acid sequence that encodes a wild-type TXAS, so that TXAS is expressed in vivo by the cells of the subject that have been transfected with said polynucleotide. Accordingly, said method leads to an overexpression of wild-type TXAS which compensates expression of defective mutated TXAS. The administered polynucleotide does not contain a mutation selected in the group consisting of 1463T>C, 248T>C, 1444G>T and 1238G>A.

The invention also relates to the use of a TBXAS1 polynucleotide for the manufacture of medicament intended for the treatment of a disease associated with an increased bone mineral density. Preferably said TBXAS1 polynucleotide is administered in a therapeutically effective amount.

Preferably the TBXAS1 polynucleotide sequence according to the invention is associated with elements that enable for regulation of its expression, such as a promoter sequence.

Such a nucleic acid may be in the form of a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The TBXAS1 polynucleotide may be introduced into a target cell by means of any procedure known for the delivery of nucleic acids to the nucleus of cells, ex vivo, on cells in culture or removed from an animal or a patient, or in vivo.

Ex vivo introduction may be performed by any standard method well known by one skilled in the art, e.g. transfection, electroporation, microinjection, transduction, cell fusion, DEAE dextran, calcium phosphate precipitation, or use of a gene gun.

The TBXAS1 polynucleotide can also be introduced ex vivo or in vivo by lipofection. In certain embodiments, the use of liposomes and/or nanoparticles is contemplated for the introduction of the donor nucleic acid targeting system into host cells.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core.

Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes (Feigner et al., 1989).

Alternatively, one of the simplest and the safest way to deliver TBXAS1 polynucleotide across cell membranes in vivo may involve the direct application of high concentration free or naked polynucleotides (typically mRNA or DNA). By "naked DNA (or RNA)" is meant a DNA (RNA) molecule which has not been previously complexed with other chemical moieties. Naked DNA uptake by animal cells may be increased by administering the cells simultaneously with excipients and the nucleic acid. Such excipients are reagents that enhance or increase penetration of the DNA across cellular membranes and thus delivery to the cells delivery of the therapeutic agent. Various excipients have been described in the art, such as surfactants, e.g. a surfactant selected form the group consisting of Triton X-100, sodium dodecyl sulfate, Tween 20, and Tween 80; bacterial toxins, for instance streptolysin O, cholera toxin, and recombinant modified labile toxin of $E$ $coli$; and polysaccharides, such as glucose, sucrose, fructose, or maltose, for instance, which act by disrupting the osmotic pressure in the vicinity of the cell membrane. Other methods have been described to enhance delivery of free polynucleotides, such as blocking of polynucleotide inactivation via endo- or exonucleolytic cleavage by both extra- and intracellular nucleases.

Alternatively, the invention also provides a method for treating or preventing a disease associated with an increased bone mineral density which comprises the step of administering a subject in need thereof with a wild-type TXAS.

The administered TXAS polypeptide may be a variant of the wild-type TXAS, provided that the polypeptide retains the activity to convert prostaglandins (PG) H2 into Thromboxane A2 (TXA2). Accordingly; the polypeptide does not comprise a mutation selected from the group consisting of mutations which result in Leu488Pro, Leu83Pro, Gly482Trp and Arg413Glu mutants of TXAS.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides of the invention can be use in an isolated (e.g., purified) form or contained in a vector, such as a membrane or lipid vesicle (e.g. a liposome).

Alternatively, the invention also provides a method for treating or preventing of a disease associated with an increased bone mineral density which comprises the step of administering a subject in need thereof with Thromboxane A2 or an analog thereof. Thromboxane A2 has a bicyclic oxaneoxetane structure as follows:

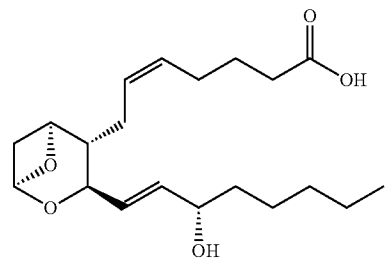 [SMILES: CCCCC[C@H](O)/C=C/[C@H]1O[C@H]2C[C@H](O2)[C@@H]1C/C=C\CCCC(=O)O]

The analog of thromboxane A2 may consist for example in U46619 (9,11-dideoxy-9α,11α-methanoepoxy $PGF_{2α}$; 9,11-dideoxy-9α,11α-methanoepoxy Prostaglandin $F_{2α}$ (CAS 56985-40-1)) which as a structure as follows:

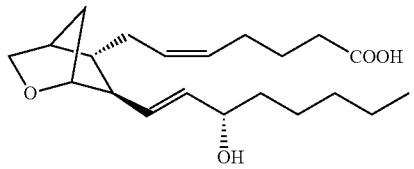 [SMILES: CCCCC[C@H](O)/C=C/[C@H]1C2CC(CO2)[C@@H]1C/C=C\CCCC(=O)O]

The invention further provides methods for treating or preventing a disease associated with a decreased bone mineral density. Examples of such diseases include but are not limited to osteoporosis, osteoporosis associated to atherosclerosis, osteoporosis associated to pseudoglioma, osteoporosis and oculocutaneous hypopigmentation syndrome, osteoporosis due to endocrinological dysfunction, osteogenesis imperfecta, bone metastasis and primitive bone cancers osteosarcoma.

In particular embodiment, the invention relates to a method for the treatment of a disease associated with decreases bone mineral density which comprises the step of administering a subject in need thereof with an inhibitor of expression of TBXAS1 gene expression.

Inhibitors of TBXAS1 gene expression for use in the present invention may be based on anti-sense oligonucleotide constructs. Anti-sense oligonucleotides, including anti-sense RNA molecules and anti-sense DNA molecules, would act to directly block the translation of TBXAS1 mRNA by binding thereto and thus preventing protein translation or increasing mRNA degradation, thus decreasing the level of TXAS, and thus activity, in a cell. For example, antisense oligonucleotides of at least about 15 bases and complementary to unique regions of the mRNA transcript sequence encoding TXAS can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of TBXAS1 gene expression for use in the present invention. TBXAS1 gene expression can be reduced by contacting a subject or cell with a small double stranded RNA (dsRNA), or a vector or construct causing the production of a small double stranded RNA, such that TBXAS1 gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of TBXAS1 gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of TBXAS1 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of TBXAS1 gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing TBXAS1 gene. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUCI9, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Alternatively, the invention also provides a method for treating or preventing a disease associated with a decreased bone mineral density which comprises the step of administering a subject in need thereof with a thromboxane inhibitor.

Contemplated thromboxane inhibitors for use in the present invention include, for example, 2-(acetyloxy)-benzoic acid, AA 2414 (seratrodast, (4-hydroxy-(Z)-(2,4,5-trimethyl-3,6-dioxo-1,4-cyclohexadien-1-yl)-benzeneheptanoic acid), AH 2,848 ((1[alpha](Z), 2[beta],5[alpha])-(+-)-7-(5-(((1,1'-biphenyl)-4-yl)methoxy)-2-(4-morpholinyl)-3-oxocyclopentyl)-4-heptenoic acid), BAY u3405 (ramatroban, 3R-((4-fluorophenyl)sulfonyl)amino)-1,2,3,4-tetrahydro-9H-carbazole-9-propanoic acid), BM 13177 (sulotroban, ((4-(2-((phenylsulfonyl)amino)ethyl) phenoxy)-acetic acid), BM 13505 (daltroban, (4-(2-(((4-chlorophenyl)sulfonyl)amino)ethyl)-benzeneacetic acid), BMS 180291 (ifetroban, ((+)-1S-(1[alpha],2[alpha],3[alpha],4[alpha])-2-((3-(4-(n-pentylamino)carbonyl)-2-oxazolyl)-7-oxabicyclo)(2.2.1)hept-2-yl)methyl)benzene proponic acid), cinnamorphilin ((8R,8'S)-4,4'-dihydroxy-3,3'-dimethoxy-7-oxo-8,8'-neolignan), CGS 12970 (3-methyl-2-(3-pyridyl)indole-1-octanoic acid), CGS 15435, CGS 22652 (4-(((4-chlorophenyl)sulfonyl)amino)butyl)-3-pyridineheptanoic acid), CV 4151 ((E)-7-phenyl-7-(3-pyridinyl)-6-heptenoic acid), dazoxiben (4-(2-(1H-imidazol-1-yl)ethoxy) benzoic acid), dazmegrel, DT-TX 30 ((E)-6-(4-2-(4-chlorobenzene sulphonylamino)ethyl)phenyl)-6-(3-pyridyl)-hex-5-enoic acid), etofibrate (2-(2-(4-chlorophenoxy)-2-methyl-1-oxopropoxy)-3-pyridinecarboxylic acid ethyl ester), EP 045 ((1 [alpha],2[beta](Z),3[alpha],4[alpha])-7-(3-((((phenylamino) carbonyl)hydrazono)methyl)bicyclo(2.2.1) hept-2-yl), EP 092 (7-((1S,2S,3S,4R)-3-(1-(3-(phenylthioureidoimino) ethyl)-bicyclo(2.2.1)heptane-2-yl)-5-heptenoic acid), F 10171 (1-(((5-(4-chlorophenyl)-2-furanyl)methylene) amino)-3-(4-(1-piperazinyl)butyl)-2,4-imidazolidinedione), FCE 27262 ((E)-(+-)-5-(((1-cyclohexyl-2-(1H-imidazol-1-yl)-3-phenylpropylidene)amino)oxy-pentanoic acid), FI 2845 (camongrel, 2,3-dihydro-5-(2-(1H-imidazol-1-yl) ethoxy)-indene-1-carboxylic acid), FK 070 ((5Z)-6-((2S, 4R)-4-((4-chlorophenyl)sulfonyl)amino)-1-(3-pyridinylmethyl)-2-pyrrolidinyl)-5-hexenoic acid monohydrate), furegrelate, GR 32191 (vapiprost, (1R-(1[alpha](Z),2[beta],3[beta],5[alpha]))-(+)-7-(5-((1,1'-biphenyl)-4-ylmethoxy)-3-hydroxy-2-(1-piperidinyl)cyclopentyl)-4-++++heptonoic acid), GR 83783 (1[alpha](Z),2[beta],5[beta])-6-((2-(hexahydro-1H-azepin-1-yl)-5-((4-(4-propyl-3-pyridinyl)phenyl) methoxy)cyclopentyl)oxy)-4-hexanoic acid), GR 85305 ((5E)-6-(3-(2-((4-iodophenyl)sulfonyl)amino)ethyl)phenyl)-6-(3-pyridinyl)-5-hexenoic acid), GR 108774 ((5E)-6-(3-(2-((4-iodophenyl)sulfonyl)amino)-1,1-dimethylethyl) phenyl)-6-(3-pyridinyl)-5-hexenoic acid), IBI P-05006 (2-(6-carboxyhexyl)-3-n-hexylcyclohexyl amine), isbogrel ((E)-7-phenyl-7-(3-pyridinyl)-6-heptenoic acid), ICI 180080 (5(Z)-7-(2,2-dimethyl-4-(2-hydroxyphenyl)-1,3-dioxan-cis-5-yl)heptenoic acid), ICI-192605 ((Z)-(2[alpha],4[alpha]5[alpha])-6-(2-(2-chlorophenyl)-4-(2-hydroxyphenyl)-1,3-dioxan-5-O-4-hexenoic acid), KT 2962 (3-(4-(((4-chlorophenyl)sulfonyl)amino)butyl)-6-(1-methylethyl)-1-azulenesulfonic acid monosodium salt), KY 234 ((E)-11-(2-(5,6-dimethyl-1H-benzimidazol-1-yl)-6,11-dihydro-dibenz (b,e) oxepin-2-carboxylic acid sodium salt), KW 3635 (sodium (E)-11-(2-(5,6-dimethyl-1-benzimidazolyl)ethylidene)-6,11-dihydrodibenz(b,e)oxepin-2-carboxylate monohydrate), linotroban (4-methyl-benzenesulfonate-N-((phenylmethoxy)carbonyl)-serine ethyl ester), L 640035 (dibenzo(b,f)thiepin-3-methanol-5,5-dioxide), L 670596 ((-)-6,8-difloro-2,3,4,9-tetrahydro-9-((4-(methylsulfonyl) phenyl)methyl)-1H-carbazole-1-acetic acid), L 636499 ((5, 5-dioxide-dibenzo(b,f)thiepin-3-carboxylic acid), L 655240 (3-methyl-1-((4-chlorophenyl)methyl)-5-fluoro-[alpha],[alpha],-1H-indole-2-propanoic acid), midazogrel, ON 579 ((4-((2-(((4-chlorophenyl)sulfonyl)amino)ethyl)thio)-2,6-difluoro phenoxy)acetic acid), ONO 3708 ((1S-(1[alpha],2[beta](Z),3[alpha](S),5[alpha]))-7-(3-((cyclopentyl hydroxyacetyl)amino)-6,6-dimethylbicyclo (3.1.1hept-2-yl)-5-heptenoic acid), OKY 046 (ozagrel hydrochloride, (E)-3-(4-(1H-imidazol-1-ylmethyl)phenyl)-2-propenoic acid monohydrochloride), OKY 1555, OKY 1580, OKY 1581, (E)-2-methyl-3-(4-(3-pyridinylmethyl)phenyl)-2-propenoic acid sodium salt), S-145 ((+-)-(5Z)-7-(3-endo-((phenylsulfonyl)amino)bicyclo(2.2.1)hept-2-exo-yl)heptenoic acid), picotamide (4-methoxy-N—N'-bis(3-pyridinylmethyl)-1,3-benzenedicarboxamide monohydrate), R 68070 (ridogrel, (E)-5-(((3-pyridinyl(3-(trifluoromethyl)phenyl) methylene)amino)oxy)-pentanoic acid), S-1452 (domitroban, (1R)-(1[alpha]2[alpha](Z),3[beta],4[alpha]))-7-(3-((phenylsulfonyl)amino)bicyclo (2.2.1)hept-2-yl)-5-heptenoic acid), SKF 88046 (N-7-(3-chlorophenyl)-N2-((7-(((3-chlorophenyl)amino)sulfonyl)-3,4-dihydro-2(1H)-isoquinolinyl)sulfonyl)-3,4-dihydro-2,7(1H)-isoquinol disulfonamide), SQ 27427 (((1S)-(1[alpha],2[alpha](Z),3 [alpha](1E,3R),4[alpha]))-7-(3-(3-cyclohexyl-3-hydroxy-1-propenyl)-7-oxabicyclo(2.2.1)hept-2-yl)-5-heptenoic acid), SQ 28668 ((1[alpha],2[alpha](Z), 3[alpha](1E,3S,4R),4[alpha]))-7-(3-(3-hydroxy-4-phenyl-1-pentyl)-7-oxabicyclo (2.2.1)hept-2-yl)-5-heptenoic acid), SQ 29548 (((1S)-(1[alpha],2[beta](5Z),3[beta],4[alpha])-7-(3-((2-((phenylamino)-carbonyl)hydrazino)methyl)-7-oxabicyclo (2.2.1)-hept-2-yl)-5-heptenoic acid), SQ 30741 (((1S)-(1 [alpha],2[alpha](Z),3[alpha],4[alpha]))-7-(3-(((((1-oxoheptyl)amino)acetyl)amino)methy)-7-oxabicyclo (2.2.1)-hept-2-yl)-5-heptenoic acid), SQ 33961 ((1-exo, exo))-2-((3-(4-(((4-cyclohexylbutyl)amino)carbonyl)-2-oxazolyl)-7-oxabicyclo(2.2.1)-hept-2-yl)methyl)-benzenepropanoic acid), TER 930180 (4-1-(((4-chlorophenyl)sulfonyl)amino)methyl)-4-(3-pyridinyl)

butyl)-benzenepropanoic acid), UK 34787, UP 11677 (mipitroban ([beta],[beta]-dimethyl-6-chloro-3-((4-chlorophenyl)methyl)-3H-imidazo[4,5-b]pyridine-2-butanoic acid), Y 20811, YM 158 ((3-((4-tert-butylthiazol-2-yl)methoxy)-5'-(3(4-chlorobenzenesulfonyl)propyl-2'-(1-tetrazol-5-ylmethoxy)benzanilide monosodium salt monohydrate), Z 335 ((+−)-sodium(2-(4-(chloro phenylsulfonyl aminomethyl)indan-5-yl)acetate monohydrate), ZD 1542 (4(Z)-6-(2S,4S,5R)-2-(1-methyl-1-(2-nitro-4-tolyloxy) ethyl)-4-(3-pyridyl)-1,3-dioxan-5-yl)hex-4-acid), ZD 9583 ((4Z)-6-((2S,4S,5R)-2-(1-(2-cyano-4-methylphenoxy)-1-methylethyl)-4-(3-pyridyl)-1,3-dioxan-5-yl)hex-4-enoicn acid).

Although the above compounds are collectively referred to as "thromboxane inhibitors", one skilled in the art will readily recognize whether any particular compound is specifically a thromboxane A2 receptor antagonist, a thromboxane synthase inhibitor or a dual-acting thromboxane receptor antagonist and thromboxane synthase inhibitor.

Dual-acting thromboxane receptor antagonist and thromboxane synthase inhibitor may be also selected from the group consisting of terbogrel, picotamide and derivatives of oxazolecarboxamide-substituted [omega]-phenyl-[omega]-(3-pyridyl)-alkenoic acid including compounds as disclosed in EP 0811621, EP 0816361 and U.S. Pat. No. 5,990,308. Terbogrel is a pyridine derivative of the formula

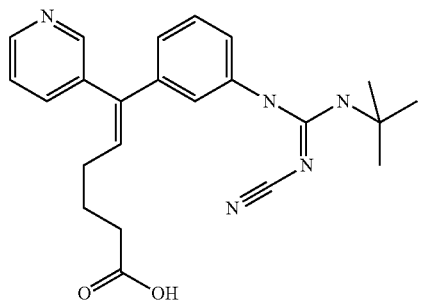 [SMILES: CC(C)(C)N/C(=N/C#N)Nc1cccc(/C(=C/CCCC(=O)O)c2cccnc2)c1]

which chemical name is (5E)-6-[3-[[(cyanoamino)[(1,1-dimethylethyl)amino]-methylene]amino]phenyl]-6-(3-pyridinyl)-5-hexenoic acid and which is described in EP 547517 for example.

Another suitable thromboxane synthase inhibitor is Ozagrel which is a 1-alkyl imidazole derivative that acts as a selective inhibitor of TXAS with an IC50 of 11 nM. Ozagrel has the formula as follows:

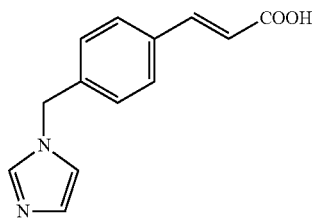 [SMILES: O=C(O)/C=C/c1ccc(Cn2ccnc2)cc1]

Suitable thromboxane inhibitors, are also described in WO 01/87343, JP7179425, JP62010072, JP2004043380, U.S. Pat. No. 5,468,757, U.S. Pat. No. 5,550,118, U.S. Pat. No. 5,604,236, and U.S. Pat. No. 5,246,956, the disclosures of which are incorporated herein by reference in its entirety.

The compounds of the invention may be combined with pharmaceutically acceptable excipients, and optionally sustained-release matrices, such as biodegradable polymers, to form therapeutic compositions.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The compounds of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

Compounds of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Screening Methods

The invention provides also methods for screening candidate compounds (e.g., polypeptides, polynucleotides or small molecules or other drugs) which may be useful for the treatment of bone mineral density related diseases.

More particularly, the invention provides methods for screening compounds that may be useful for treating disease associated with an increased bone mineral density comprising the steps consisting of:
a) providing an candidate compound
b) measuring the ability of said candidate compound to enhance the activity of TXAS
c) selecting the candidate compound which is able to enhance the activity of TXAS.

Alternatively, the invention provides methods for screening compounds that may be useful for treating disease associated with a decreased bone mineral density comprising the steps consisting of:
a) providing an candidate compound
b) measuring the ability of said candidate compound to inhibit the activity of TXAS
c) selecting the candidate compound which is able to inhibit the activity of TXAS.

The candidates compounds identified according to the methods of the invention may be then tested in a cellular model. For example, the candidate compounds may the tested for their ability to modulate the expression of Osteoprotegerin (OPG) and the ligand of the receptor activator of NE-κB (RANKL) in primary cultures osteoblasts according to the method described in Example.

The candidate compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds.

The invention will further be illustrated in view of the following figures and examples.

FIGURES

FIG. 1: Families' pedigree and skeletal x-rays of affected individuals: (a) Affected individuals of the four families from this study are in bold (b). The increased bone density in GHDD is characterised by diaphyseal involvement, abnormal long bone modelling and cortical hyperostosis.

Figure 2:
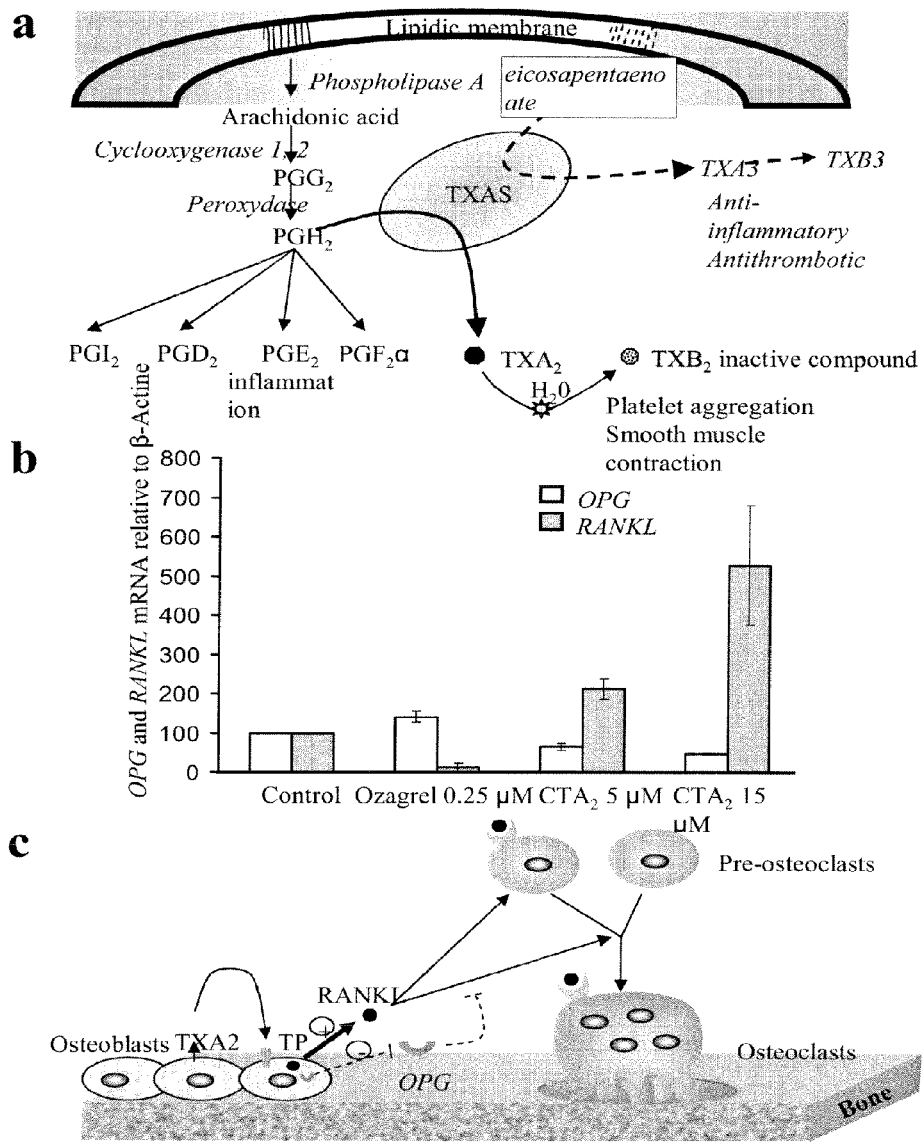

FIG. 2: TXAS/TXA2 modulate the RANKL pathway: (a) Arachidonic acid (AA) cascade. AA is mobilized in three steps: a) hormone or stress-activated mobilization of AA from the ω-6 fatty acid of the lipid bilayer of cells by phospholipases (A2 and C); b) conversion of AA to prostaglandin (PG) H2 by cyclooxygenases (COX) 1 and 2; c) isomerisation of PGH2 on ER lumen to biologically active end-products named prostanoids (i.e. PGI2, PGD2, PGE2, PGF2a and TXA2) by individual synthases. TXA3, an eicosapentanoic acid with anti-inflammatory and antithrombotic activities, is produced from mobilization of ω-3 fatty acids of the lipid bilayer. (b) RANKL and OPG expression studies. Real time quantitative PCR studies in osteoblasts showed a diminution of RANKL and an augmentation of OPG mRNA levels following inhibition of TXAS by Ozagrel. In contrast, CTA2, an analog of TXA2, led to an augmentation of RANKL and a diminution of OPG mRNA levels. (c) Schematic view of the hypothesized action of TXA2 in the induction of osteoclast differentiation/activation. TXA2 increases RANKL and decreases OPG expression in bone at least in an autocrine manner.

Figure 3:
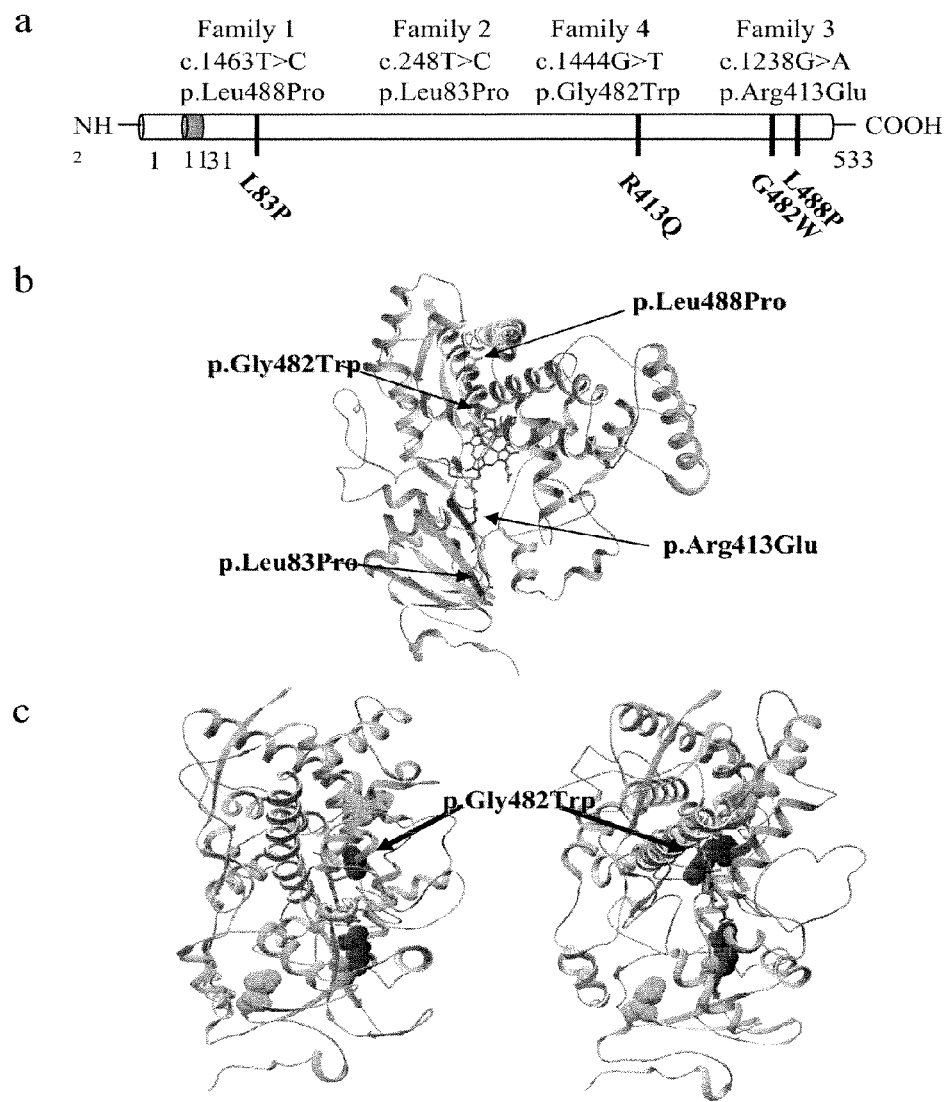

FIG. 3: Schematic representation of the human Thromboxane synthase (TXAS). (a) The location of the mutations detected in GHDD families is indicated in red and green. (b) Three dimensional Swiss-Pdb Viewer representation of TXAS. The four mutated residues were located in one of the seven β-sheet (amino acid 83, in green), in the vicinity of the heme and the enzymatic pouch (amino acids 413 and 482, in red) and in an helix α (amino acid 488, in green). (c) Swiss-Pdb Viewer representation of the van der Waals volumes of the amino acid in position 482. The glycine (left) is changed into tryptophan in family 3 (right). Note the modification of the steric hindrance at the vicinity of the catalytic site (heme in blue).

Figure 4:
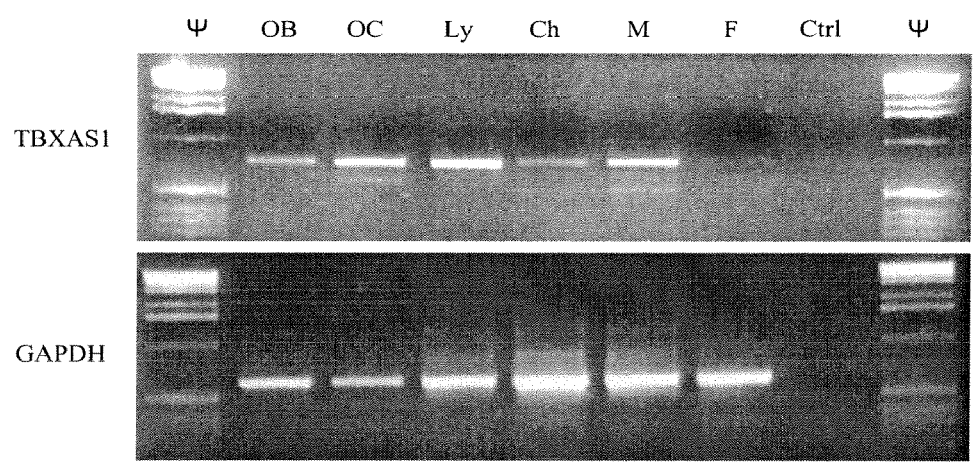

FIG. 4: Expression profile of TBXAS1: RT-PCR in human osteoblasts (OB), osteoclasts (OC), chondrocytes, muscle, human lymphoblastoid cell line and skin fibroblasts. Ψ=DNA ladder.

Figure 5:
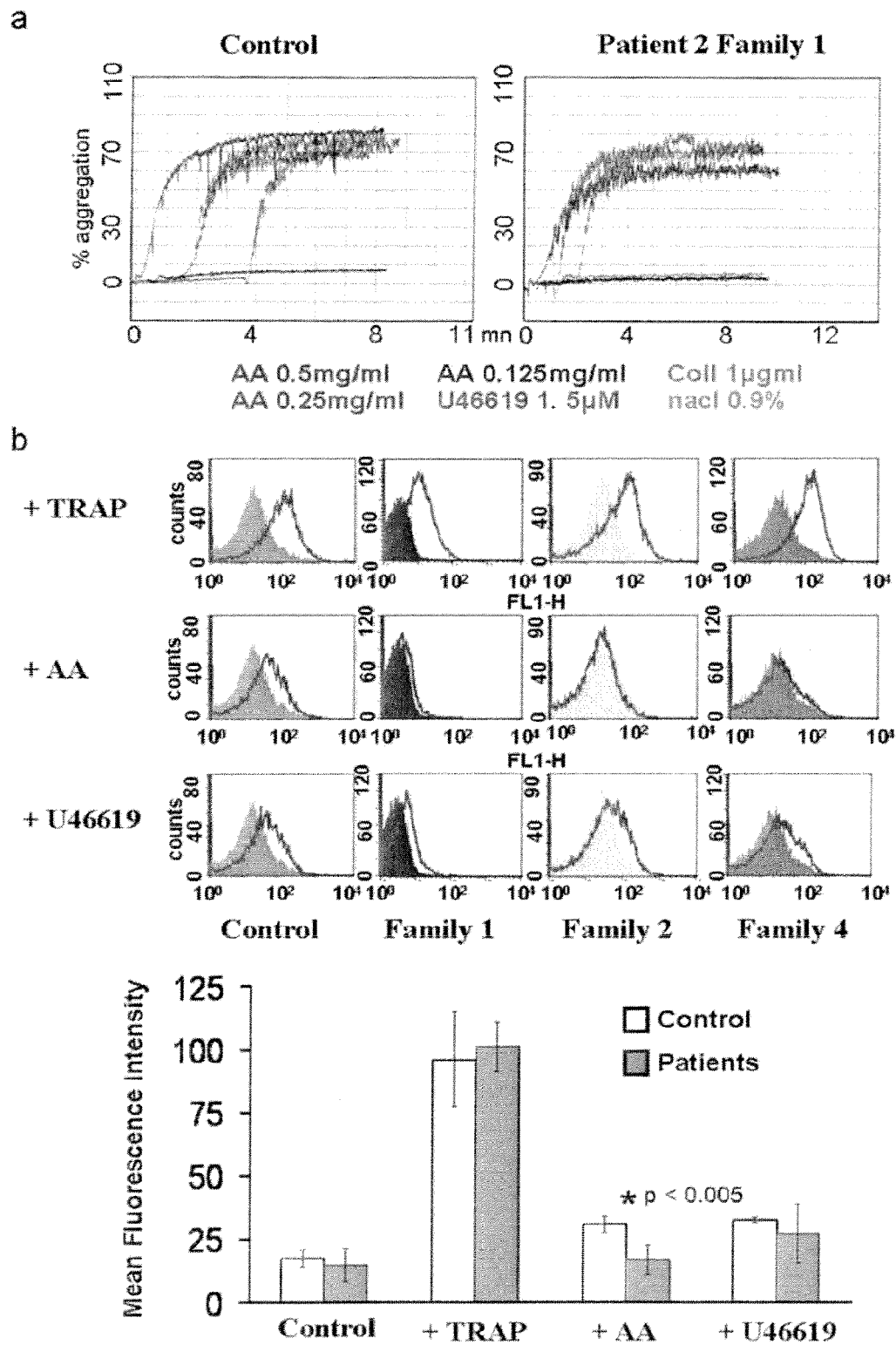

FIG. 5: Platelet studies: (a) Platelet aggregation profile in control (left) and a patient (right). Colours correspond to the various stimuli. An impaired aggregation profile was observed with the intermediate arachidonic acid concentration (AA, green) whereas, the use of U46619, an antagonist of the thromboxane receptor, led to normal platelet aggregation (light blue). (b) Platelet exocytosis studies under various stimuli. AA induced P-selectin expression was dramatically decreased (p<0.005), whereas TRAP, ADP and U46619-induced P-selectin expression was identical to controls.

TABLES

EXAMPLES

Example 1

Material & Methods

Affected Individuals:

We studied 10 affected individuals belonging to 4 inbred families. Criteria diagnostic for inclusion were: i) severe anemia requiring blood infusions and ii) skeletal changes such as diaphyseal dysplasia with increase bone density, abnormal long bone modeling, cortical hyperostosis and normal metaphyses and epiphyses. DNA samples were obtained after signed informed consent;

Mutation Detection:

A series of 17 intronic primers was designed to amplify the 4 non-coding and 13 coding exons of the TBXAS1 gene. The amplification products were purified and sequenced using the fluorescent dideoxy-terminator method on an automatic sequencer (ABI 3100)

RT-PCR:

TABLE 1

Clinical, biological and radiological findings in four GHDD families.

|  | Family 1 | | | Family 2 | | Family 3 | | Family 4 | | |
|---|---|---|---|---|---|---|---|---|---|---|
| Patient | II1 | II2 | III1 | II1 | II3 | II2 | II6 | II1 | II2 | II5 |
| Geographic origin | Algeria | | | Tunisia | | Tunisia | | Pakistan | | |
| Consanguinity | 1/16 | | | ? | | 1/32 | | 1/16 | | |
| Age at diagnosis | 34 years | 24 years | 16 months | 25 months | 18 months | 16 years | 2 years | 13 years | 13 years | 5 months |
| Gender | M | M | M | M | M | F | M | F | F | F |
| "Asymptomatic" | − | + | − | − | − | + | − | + | + | − |
| Corticosteroid therapy | + | − | + | − | + | − | + | − | − | + |
| Anemia | + | + (mild) | + | +* | +* | − | + | − | − | + |
| Thrombocytopenia | + | − | + | + | + | − | + | − | − | + |
| Thrombocytosis episodes | − | − | − | − | − | − | − | − | − | + |
| Leucopenia | − | − | − | − | − | − | − | − | − | − |
| Biological inflammation | + | − | + | − | − | − | + | − | − | + |
| Diaphyseal dysplasia | + | + | + | + | + | + | + | + | + | + |
| Mutation | c.1463T > C, p.Leu488Pro | | | c.248T > C, p.Leu83Pro | | c.1444G > T, p.Gly482Trp | | c.1238G > A, p.Arg413Glu | | |

*Spontaneous remission

TABLE 2

TXB$_2$ and PGE$_2$ levels in plasma rich platelet from GHDD patient compared to control.

|  | Before AA induction | AA 0.25 mg/ml | AA 0.5 mg/ml |
|---|---|---|---|
| TXB$_2$ levels (ng/ml) | | | |
| Patient II1 (Family 1) | 1.9 | 4.2 | 5.8 |
| Patient II2 (Family 1) | 2.27 | 3.5 | 4.3 |
| Control | 325 | 450 | 870 |
| PGE$_2$ levels (ng/ml) | | | |
| Patient II1 (Family 1) | 182.5 | 342 | 620 |
| Patient II2 (Family 1) | 50 | 580 | 625 |
| Control | 9.8 | 30.5 | 52.5 |

AA: arachidonic acid

Total RNAs were extracted from human muscle, primary culture cells (osteoblasts, chondrocytes and fibroblasts) and from cord blood cells transdifferentiation into osteoclasts using the RNeasy Mini Kit (Qiagen). cDNA were synthesized by priming with random hexamers in the presence of MuLV reverse transcriptase using the manufacturer's protocol (GeneAmp RNA PCR Core Kit, Roche). A total of 30 PCR cycles were performed at an annealing temperature of 60° C. to amplify a 772-bp fragment specific for TBXAS1 including exon 12 known to be spliced (primer sequences available on request).

Three Dimensional Structure:

The three-dimensional structure of the human Thromboxane synthase (isoform TXS-I) was modeled by comparative modeling methods and energy minimization using the program Swiss-Model in the optimized mode (Schwede, T et al. 2003). The degree of identity between TXAS and five templates (41.31%, 40.01%, 37.52%, 27.72% and 33.24% for 1W0F, 1 TQN, 2j0C, 1OG5 and 1BVY respectively) allowed us to model the structure of human TXAS using the X-ray coordinates of these templates. The 2.65 Å (PDB code 1WOF), 2.05 Å (1TQN), 2.80 Å (2J0C), 2.55 Å (1OG5) and 2.03 Å (1BVY) coordinate sets were used as templates for the structural model. The overall folding was quite similar to structurally established P450 proteins, except for two regions (amino acids 260-277 and 295-330) due to a lack of structural informations. Residues 32-534 of the submitted sequence were used to build the model. Swiss-Pdb Viewer 3.7 was used to visualize the structures and to analyze the structural insight into TXAS mutations.

Thromboxane and Prostaglandin E2 Levels:

De novo levels of TXB2 and PGE2 production in plasma rich platelet before and after AA induction were directly determined in patients II1 and II2 from family 1 by Enzyme-linked immunosorbent assay (ELISA) (Cayman chemical ref 519031.1 and 514010.1, Ann Arbor, Mich.) and compared to sex and age match control. ELISA data were analysed using Revelation software V4.22 (Dynec technology).

Platelet Aggregation Tests:

Aggregation studies were performed within 2 hours of blood collection, at 37° C., by using a photometric method on a 4-channel aggregometer (Regulest, Amneville, France) (Dupont, A. et al. 2003). Briefly, a 280-µL aliquot of platelet-rich plasma was incubated for 3 minutes at 37° C. and was then stirred at 1100 rpm for 2 minutes before adding 20 µL of saline or following agonists: arachidonic acid 1.5, 0.75 and 0.375 mmol/L (Helena), ADP 2, 5 and 10 µmol/L (Sigma Aldrich), U46619 1.5 µmol/L (Calbiochem) and collagen 1 µg/mL (Horm). Platelets aggregate when the agonist is added, thereby leading to an increase in light transmission, which is recorded for 5 min. Aggregation was expressed as the maximal percent change in light transmission from baseline, using platelet-poor plasma as reference (arbitrarily 100%).

Analysis of Platelet Glycoproteins and Platelet Activation by Flow Cytometry:

Surface expression of platelet glycoproteins GPIb (CD42b), GPIIIa (CD61) and P-selectin (CD62P) before and after activation was performed in plasma rich platelet by flow cytometry using a FACSCalibur cytometer (Becton Dickinson) and using Platelet GP Receptors (Biocytex) according to the manufacturer instructions (Hezard, N. et al. 2003). Activation was achieved using TRAP (50 µM, 25 µM, 12.5 µM, NeoMPS), arachidonic acid (0.5 mg/mL, Sigma), U46619 (5 µM, VWR Calbiochem). Results are expressed in percentage of the mean fluorescence intensity (MFI) at the surface of patient's platelets compared to the MFI at the surface of a control studied in the same conditions. Change in P-selectin expression induced by agonists is expressed in MFI.

Osteoblasts Culture and Real-Time Quantitative PCR:

Human normal cranial suture were obtained after signed informed consent during routine surgery for craniosynostosis. Osteoblasts were cultured in Dulbecco's modified Eagle medium (with 10% fetal bovine serum) as described elsewhere (De Pollack, C. et al. 1996). Ozagrel (Cayman Chemical) was daily added at 0.25 µM (IC50 of 11 nM) in culture media during 3 days and CTA2 (Cayman Chemical) was added at day one in culture media at two concentrations (5 µM and 15 µM). Cells were harvested at day 3. Real-time quantitative PCR using Light Cycler technology (Roche Manheim) was performed for OPG and RANKL mRNA in each sample. The experiments were performed five times. In each experiment, samples were run in triplicate. The amounts of OPG and RANKL mRNA were normalized to the amount of β-actin mRNA. Student test was used for p values determination.

Results:

GHDD (OMIM 231095) is a rare autosomal recessive disorder characterized by increased bone density (IBD) disorder with predominant diaphyseal involvement and aregenerative corticosensitive anemia (Ghosal et al. 1988). Studying two consanguineous GHDD families from Algeria and Tunisia, we recently mapped the disease gene to chromosome 7q33-q34 (Isidor B. et al. 2007). Here, we ascribe GHDD to mutations in the thromboxane synthase gene (TBXAS1) in these families and in two additional families of Tunisian and Pakistanese origin (FIG. 1).

IBD is caused by an imbalance between bone resorption and bone formation. Among the 36 genes of our 3.84 Mb region, we first considered 25 genes by their function and excluded them by direct sequencing. Although TBXAS1 is thought to be responsible for a mild bleeding disorder in human (Mestel F. et al. 1980; Weiss H J. Et al. 2002), this gene was then regarded as a candidate gene based on its putative involvement in osteoclast recruitment (Gruber R. et al. 2002). TBXAS1 (17 exons, 4 non-coding and 13 coding exons) encodes a 60-kDA transmembrane thromboxane synthase (TXAS), considered as an atypical member of the cytochrome p450 superfamily as it lacks mono-oxygenase activity. TXAS is one of the terminal enzymes of the arachidonic acid (AA) cascade and converts prostaglandins (PG) H2 into Thromboxane A2 (TXA2) in the endoplasmic reticulum lumen. TXA2 belongs to the group of eicosanoids produced by nearly all cells and involved in inflammation, vasoconstriction/vasodilatation, coagulation, pain, and fever (Shen R F. et al. 1998). Eicosanoids are produced by conversion of AA (from the ω-6 fatty acids of the lipid bilayer) by cyclooxygenases (COX 1-2) and isomerisation into biologically active end products by individual synthases (Shen R F. et al. 1998) (FIG. 2a). TXA2 is a powerful inducer of platelet aggregation and a constrictor of vascular/respiratory smooth muscle.

Direct sequencing of the TBXAS1 gene detected distinct homozygous missense mutations in all four GHDD families (c.1463T>C, c.248T>C, c.1444G>T and c.1238G>A, FIG. 1, FIG. 3 and Table 1). The mutations involved conserved amino acids across species and ¾ were located near residues involved in the heme binding domain. They cosegregated with the disease and were not identified in 210 control chromosomes. RT-PCR analysis detected TBXAS1 transcripts in human osteoblasts (OB), osteoclasts (OC), chondrocytes, muscle, lymphoblastoïd cell lines and to a lesser extent in skin fibroblasts (FIG. 4).

Because TXAS is an intrinsic membrane protein, a detergent treatment is required for purification and its structural analysis is difficult to achieve. Thus, the functional consequences of the mutations were investigated by three dimensional structure modelling via alignment of the TXAS sequence with other P450 family members. The model obtained is shown as a Swiss-Pdb Viewer representation (FIG. 3a). The four mutated residues were located in one of the seven β-sheets (amino acid 83), in the vicinity of the heme, in the enzymatic pouch (amino acids 413 and 482) and in an helix α (amino acid 488).

Because TXA2 plays a key role in platelet aggregation ((Shen R F. et al. 1998), we investigated primary hemostasis in our patients. No history of spontaneous or excessive bleeding after surgery was reported and primary hemostasis in patients II2, II3 and II6 (Families 1, 2 and 3 respectively) was normal (Ivy test) (Table 1). Patient II2 of family 1 was eligible for platelet aggregation analysis, as he was not receiving any medication that could interfere with aggregation tests. An impaired aggregation profile was observed using intermediate AA concentrations (4%), whereas two age and sex-matched controls showed respective values of 80 and 90% (FIG. 5a). Aggregation induced by either low or high AA concentrations and other agonists gave similar results in patient II2 and in controls. In particular, aggregation induced by U46619, a specific agonist of TXA2 receptor was normal in patient II2 (family 1). We also studied platelet exocytosis under different stimuli. Expression of platelet GPIb, GPIIIa and P-selectin prior to activation fell within normal ranges in five GHDD patients (75-156%, data not shown). Finally, we studied P-selectin expression before and after various stimuli in three GHDD patients. AA induced P-selectin expression was dramatically decreased ($p<0.005$), whereas TRAP, ADP and U46619-induced P-selectin expression was identical to controls (FIG. 5b).

TXB2 and PGE2 ELISA assay in plasma rich platelet (PRP) revealed low TXB2 levels in patients before AA induction and no significant variation of TXA2 levels after AA induction compared to control (100 and 200 folds less respectively). By contrast, PRP PGE2 levels before AA induction were higher in patients compared to control with a wide range of variability (5-18 folds more than control). Interestingly, the response to AA induction was more intense in GHDD patient PRP than in control. (Table 2).

In order to elucidate the mechanism of IBD in GHDD, we investigated the role of TXAS and TXA2 on expression of RANKL, the ligand of the receptor activator of NF-κB and osteoprotegerin (OPG) in primary cultured osteoblasts (OB) derived from normal human sutures. Addition of Ozagrel, a specific inhibitor of TXAS, to culture media dramatically decreased RANKL expression but increased OPG expression, compared to control values (−78%, $p<0.005$ and +50%, $p<0.005$ respectively). Addition of CTA2, a stable analog of TXA2, had an opposite effect with an increase of RANKL (+94%, $p<0.005$ and +471%, $p<0.03$ at 5 μM and 15 μM respectively) and a decrease of OPG expression (−40%, $p<0.005$ and −53%, $p<0.005$ at 5 μM and 15 μM respectively) (FIG. 2b).

Here, we report the identification of TBXAS1 mutations in a human disorder combining bone and hematological anomalies. The four missense mutations involved amino acids which are crucial for enzyme activity. A change of the arginin at position 413 (p.Arg413Lys), also involved in family 3 (p.Arg413Glu) has been shown to account for a decreased TXAS activity (1%) with a decreased heme content of the enzyme (30%) (Hsu P Y. et al. 2000). The mutation p.Gln482Trp (family 4) changed an aliphatic amino acid with low steric hindrance into an aromatic acid with high steric hindrance in the vicinity of the catalytic site. Such a modification of the steric hindrance may modify the interaction of the enzyme/substrate complex (i.e. TXAS and PGH2) (FIG. 3b). Finally, the leucine to proline changes at positions 83 (β-sheet) and 488 (α-helix) may introduce a coil in the quaternary structure of TXAS.

Although GHDD patients do not have any bleeding problems, in vitro studies revealed a lack of platelet aggregation after AA induction presumably due to a decreased TXAS enzyme activity and a defect in TXA2 production, confirming that TXA2 is a key factor of platelet aggregation. However, the absence of bleeding disorder in our patients is suggestive of a redundant mechanism for platelet aggregation. Similarly, invalidation of tbxas1 in mouse does not lead to a spontaneous bleeding disorder, a feature ascribed to the TXA2-independent platelet aggregation induced by thrombin and collagen (Yu I S. et al. 2004).

Whereas high levels of TXA2 are observed in arterial hypertension (Shen R F. et al. 1998), blood pressures of the patients from this study were normal (Table 1).

Aregenerative corticosensitive anemia and inflammation are other features observed in GHDD patients. These features might be related to high PGE2 levels. Indeed, PGE2 has been involved in various cellular functions including inflammation (Davies P. et al. 1984) and in vitro studies have shown its ability to suppress the growth of late erythroid progenitor cells (Taniguchi S. et al. 1989). However, anemia and inflammation are not consistently observed in all patients and quite variable in severity. This variability might be related to the variable interindividual production of PGE2.

Because IBD is a major feature in GHDD, one can hypothesize that TXAS/TXA2 also plays a key role in an as yet unknown function, namely bone remodeling. Eicosanoids have important physiological/pathological roles in skeletal metabolism (Pilbeam C C. et al. 2002). Among them, PGE2 is known to both stimulate bone resorption and particularly enhances cortical bone mass, suggesting a complex mechanism for PGE2-induced bone remodeling dependent from EP2 and EP4 receptors (Raisz L G. et al. 2003). In addition, long-term PGE2 infusion in human is responsible for a dose dependent hyperostosis (Jorgensen H R. et al. 1988).

A stable analog of TXA2 (CTA2) is also involved in the recruitment and maturation of osteoclasts in bone marrow cultures via the osteoblastic RANKL pathway (Gruber R. et al. 2002). Our data shows that i) CTA2 increased RANKL and decreased OPG levels in a dose-response manner, and ii) inhibition of TXAS by Ozagrel produced the opposite effect (FIG. 2b). The finding of a direct link between RANKL/OPG expression and TXAS activity supports the view that TXA2 controls induction of osteoclast differentiation/activation in an autocrine manner in osteoblasts (FIG. 2c). In addition to the TXAS/TXA2 effect on bone remodeling, the interindividual variable production of PGE2 may also account for the variability of bone manifestations in GHDD.

Most of the genes causing IBD are involved in osteoclast and osteoblast function/differentiation. Interestingly, several of these genes are regarded as candidate genes in bone mineral density variation (Ralston S H. et al. 2006). Moreover, estrogen and progesterone reduce expression of thromboxane receptor while an excessive amount of omega-6 fatty acid in alimentation is believed to lead to osteoporosis (Watkins B A. et al. 2001). Thus, thromboxane synthase plays a role in the pathogenesis of bone mineral density variation and osteoporosis. In conclusion, the identification of TBXAS1 mutations in GHDD demonstrates an as yet unknown function of TXAS/TXA2 in bone remodeling, with a major impact on peak bone mass variation.

Example 2

In this example, several thromboxane inhibitors are tested for their ability to treat diseases associated with a decreased bone mineral density, in various models and in human patients.

Thomboxane Inhibitors
  Ozagrel is a thromboxane synthase inhibitor (Cayman Chemical) It is administered orally to adults at a dosage of 800 mg/day.
  Picotamide is a dual-acting thromboxane receptor antagonist and thromboxane synthase inhibitor (Plactidil®, from Novartis). It is administered orally to adults, twice per day, at a dose of 600 mg.

Seratrodast is a thromboxane receptor antagonist (Takeda, Abott). It is administered orally to adults at 80 mg/day.

Diseases Associated with a Decreased Bone Mineral Density

1) In Vitro Model

Primary cultures of human osteoblasts are cultured in the presence or absence of the thromboxane inhibitors.

The following variables are measured:
levels of TCB2 are assayed by ELISA;
levels of RANKL/OPG are assayed by quantitative PCR;
PAL levels;
Cell growth of osteoblasts.

2) Animal Model: Ovariectomized Rats

This animal model is frequently used to modelize the most frequent cause of osteoporosis in women, post-menopause osteoporosis.

Female rats, aged minimum 6 months (6 per group), are ovarictomized and subjected to different treatments: untreated group, control group treated with raloxifene (Evista®) and bisphosphonates, a reference treatment for osteoporosis, group treated with ozagrel, group treated with picotamide, group treated with seratrodast. They are compared to a non-ovariectomized group for the following variables:

Bone Densitometry (BD)
  bone densitometry measured by quantitative computerized tomography (OCT). This test measures the volumetric BD (expressed in grams of hydroxyapatite per $cm^3$) and the bone geometry (diameter, cortical thickness, cortical and trabecular section surface);
  DXA-type densitometry (dual energy X-ray absorptiometry). This test measures the surfacic BD (expressed in g per $cm^2$).
Trabecular histology.
Osteoblast proliferation (in primary cultures).
Osteoblast function (in primary cultures).
Calcium incorporation (in primary cultures).

3) Clinical Study

A cohort of patients from the Bone Disease Reference Center ("Centre de Référence Maladie Osseuse") of Cochin/Lariboisière, Paris, France is randomly assigned to treatment groups (placebo, Evista® and bisphosphonates reference treatment, ozagrel, picotamide or seratrodast).

The efficacy of the treatment is evaluated by DXA-type densitometry.

Altogether, these studies demonstrate that inhibitors of thromboxane synthase can be successfully used for the treatment of a disease associated with decreased bone density.

REFERENCES

Throughout this application, various references describe the state of the art to which this invention pertains. The disclosures of these references are hereby incorporated by reference into the present disclosure.

Antonarakis et al., Diagnosis of genetic disorders at the DNA level, N. Engl. J. Med. 1989, 320:153-163

Arden N K, Spector T D. Genetic influences on muscle strength, lean body mass, and bone mineral density: a twin study. J Bone Miner Res. 1997 December; 12(12): 2076-81.

Barbas C F, Bain J D, Hoekstra D M, Lerner R A. (1992), Semisynthetic combinatorial antibody libraries: a chemical solution to the diversity problem. PNAS USA, 89, 4457-4461.

Brummelkamp T R, Bernards R, Agami R. A system for stable expression of short interfering RNAs in mammalian cells. Science. 2002 Apr. 19; 296(5567):550-3.

Colas P, Cohen B, Jessen T, Grishina I, McCoy J, Brent R. (1996) Genetic selection of peptide aptamers that recognize and inhibit cyclin-dependent kinase 2. Nature, 380, 548-50.

Cooper et al. (1991) Diagnosis of genetic disease using recombinant DNA, 3rd edition, Hum. Genet, 87:519-560

Davies P, Bailey P J, Goldenberg M M, Ford-Hutchinson A W. The role of arachidonic acid oxygenation products in pain and inflammation. Annu Rev Immunol. 1984; 2:335-57.

De Pollack, C. Renier, D. Hott, M. & Marie, P. J. Increased bone formation and osteoblastic cell phenotype in premature cranial suture ossification (craniosynostosis). J. Bone. Miner. Res. 11:401-407 (1996).

Dupont, A. et al. An intronic polymorphism in the PAR-1 gene is associated with platelet receptor density and the response to SFLLRN. Blood. 101, 1833-1840 (2003).

Elbashir S M, Harborth J, Lendeckel W, Yalcin A, Weber K, Tuschl T. Duplexes of 21-nucleotide RNAs mediate RNA interference in cultured mammalian cells. Nature. 2001 May 24; 411(6836):494-8.

Ghosal S P, Mukherjee A K, Mukherjee D, Ghosh A K. Diaphyseal dysplasia associated with anemia. J Pediatr. 1988 July; 113(1 Pt 1):49-57.

Grompe M. The rapid detection of unknown mutations in nucleic acids (1993) Nat. Genet. 5(2):111-7

Gruber R, Karreth F, Fischer M B, Watzek G. Platelet-released supernatants stimulate formation of osteoclast-like cells through a prostaglandin/RANKL-dependent mechanism. Bone. 2002 May; 30(5):726-32.

Guéguen R, Jouanny P, Guillemin F, Kuntz C, Pourel J, Siest G. Segregation analysis and variance components analysis of bone mineral density in healthy families. J Bone Miner Res. 1995 December; 10(12):2017-22.

Hannon G J. RNA interference. Nature. 2002 Jul. 11; 418(6894):244-51.

Harlow E. et al., Antibodies: A Laboratory Manual, Cold Spring Harbor Laboratory, New York, (1988).

Hezard, N. et al. Unexpected persistence of platelet hyporeactivity beyond the neonatal period: a flow cytometric study in neonates, infants and older children. Thromb Haemost. 90, 116-123 (2003).

Hsu P Y, Tsai A L, Wang L H. Identification of thromboxane synthase amino acid residues involved in heme-propionate binding. Arch Biochem Biophys. 2000 Nov. 1; 383(1):119-27.

Isidor B, Dagoneau N, Huber C, Genevieve D, Bader-Meunier B, Blanche S, Picard C, De Vernejoul M C, Munnich A, Le Merrer M, Cormier-Daire V. A gene responsible for Ghosal hemato-diaphyseal dysplasia maps to chromosome 7q33-34. Hum Genet. 2007 April; 121 (2):269-73. Epub 2007 Jan. 3.

Jayasena S. D. (1999) Aptamers: an emerging class of molecules that rival antibodies in diagnostics. Clin Chem. 45(9):1628-50.

Jørgensen H R, Svanholm H, Høst A. Bone formation induced in an infant by systemic prostaglandin-E2 administration. Acta Orthop Scand. 1988 August; 59(4):464-6.

Kelly P J, Sambrook P N, Morrison N A, Nguyen T, Eisman J A. Genetics of osteoporosis. World Rev Nutr Diet. 1997; 80:126-44.

Kobayashi S, Inoue S, Hosoi T, Ouchi Y, Shiraki M, Orimo H. Association of bone mineral density with polymorphism of the estrogen receptor gene. J Bone Miner Res. 1996 March; 11(3):306-11.

Kohler and Milstein (1975) Continuous cultures of fused cells secreting antibody of predefined specificity. Nature; 256, 495-7.

Kuklin et al. Detection of single-nucleotide polymorphisms with the WAVE DNA fragment analysis system Genet. Test (1997-98), 1(3):201-6

McManus M T, Sharp P A. Gene silencing in mammals by small interfering RNAs. Nat Rev Genet. 2002 October; 3(10):737-47.

Mestel F, Oetliker O, Beck E, Felix R, Imbach P, Wagner H P. Severe bleeding associated with defective thromboxane synthetase. Lancet. 1980 Jan. 19; 1(8160):157.

Pilbeam, C. C. Harrison, J. R. & Raisz L. G. Chapter 54, Principle of Bone Biology. 2nd edition. Academic Press. 2002.

Raisz L G, Woodiel F N. Effects of selective prostaglandin EP2 and EP4 receptor agonists on bone resorption and formation in fetal rat organ cultures. Prostaglandins Other Lipid Mediat. 2003 July; 71(3-4):287-92.

Ralston S H, de Crombrugghe B. Genetic regulation of bone mass and susceptibility to osteoporosis. Genes Dev. 2006 Sep. 15; 20(18):2492-506.

Rubin L A, Hawker G A, Peltekova V D, Fielding L J, Ridout R, Cole D E. Determinants of peak bone mass: clinical and genetic analyses in a young female Canadian cohort. J Bone Miner Res. 1999 April; 14(4):633-43.

Sambrook, Fritsch & Maniatis, Molecular Cloning: A Laboratory Manual, Second Edition (1989) Cold Spring Harbor Laboratory Press, Cold Spring Harbor, N.Y.

Schwede, T. Kopp, J. Guex, N. Peitsch, M. C. SWISS-MODEL: An automated protein homology-modeling server. Nucleic Acids Res 31, 3381-3385 (2003).

Shen R F, Tai H H. Thromboxanes: synthase and receptors. J Biomed Sci. 1998; 5(3):153-72.

Taniguchi S, Shibuya T, Harada M, Niho Y. Prostaglandin-mediated suppression of in vitro growth of erythroid progenitor cells. Kidney Int. 1989 October; 36(4):712-8.

Tuerk C. and Gold L. (1990) Systematic evolution of ligands by exponential enrichment: RNA ligands to bacteriophage T4 DNA polymerase. Science. 3; 249(4968):505-10.

Tuschl T, Zamore P D, Lehmann R, Bartel D P, Sharp P A. Targeted mRNA degradation by double-stranded RNA in vitro. Genes Dev. 1999 Dec. 15; 13(24):3191-7.

Waterhouse P, Griffiths A D, Johnson K S, Winter G. (1993) Combinatorial infection and in vivo recombination: a strategy for making large phage antibody repertoires. Nucleic Acids Research, 21, 2265-2266.

Watkins B A, Lippman H E, Le Bouteiller L, Li Y, Seifert M F. Bioactive fatty acids: role in bone biology and bone cell function. Frog Lipid Res. 2001 January-March; 40(1-2): 125-48.

Weiss H J, Lages B A. Possible congenital defect in platelet thromboxane synthetase. Lancet. 1977 Apr. 2; 1(8014): 760-1.

Yu I S, Lin S R, Huang C C, Tseng H Y, Huang P H, Shi G Y, Wu H L, Tang C L, Chu P H, Wang L H, Wu K K, Lin S W. TXAS-deleted mice exhibit normal thrombopoiesis, defective hemostasis, and resistance to arachidonate-induced death. Blood. 2004 Jul. 1; 104(1):135-42. Epub 2004 Mar. 9.

The invention claimed is:

1. A method for treating a disease associated with a decreased bone mineral density comprising administering to a subject in need thereof a compound selected from the group consisting of a thromboxane synthase inhibitor and a thromboxane receptor antagonist, wherein said disease associated with decreased mineral density is osteogenesis imperfecta.

2. The method of claim 1, wherein said thromboxane synthase inhibitor or thromboxane receptor antagonist is selected from the group consisting of Ozagrel, Seratrodast and Picotamide.

* * * * *